United States Patent [19]
Abrams et al.

[11] Patent Number: 5,100,885
[45] Date of Patent: Mar. 31, 1992

[54] COPPER RADIOSENSITIZERS

[75] Inventors: Michael J. Abrams, Glenmore; Bradley Fontaine, Landsdowne; Christen M. Giandomenico, Exton, all of Pa.

[73] Assignee: Johnson Matthey, Inc., Valley Forge, Pa.

[21] Appl. No.: 388,040

[22] Filed: Aug. 1, 1989

[51] Int. Cl.$^5$ .............. A61K 31/555; A61K 31/60; A61K 31/69
[52] U.S. Cl. ............................. 514/184; 514/185; 514/188; 514/159; 514/64; 514/499
[58] Field of Search .............. 424/630; 514/499, 188, 514/184, 185, 159, 64

[56] References Cited
PUBLICATIONS

Kadota et al., Chem. Abstracts, 78(6), #37317v, 1972.

Primary Examiner—Thurman K. Page
Assistant Examiner—G. S. Kishore
Attorney, Agent, or Firm—Cushman, Darby & Cushman

[57] ABSTRACT

Hypoxic cells are rendered more sensitive to irradiation by subjecting the cells to treatment with a Cu(II) coordination compound.

2 Claims, No Drawings

COPPER RADIOSENSITIZERS

The present invention relates to radiosensitization and, more particularly, to a method and composition for rendering hypoxic cells more sensitive to being killed by X-rays or other forms of irradiation.

BACKGROUND TO THE INVENTION

One established method of cancer treatment comprises irradiation by high-energy electromagnetic waves, typically X-rays. Solid tumors contain significant numbers of cells which are distal from the vasculature leading to oxygen deficiency or hypoxia. Hypoxia protects cells from radiotherapy. There is, therefore, a need for compounds which render the hypoxic cells more sensitive to killing by X-rays or the like. These compounds are referred to herein as "radiosensitizers."

A variety of transition metal complexes have been shown to possess radiosensitizer activity. These include complexes of Ag, Cu, Zn, Hg, Pt, Co, Fe and Rh. For a current review, see Kirsten Skow, *Radiation Research*, 112:217-242 (1987). Copper (II) complexes have been reported possessing radiosensitizer activity and radioprotectant activity. For example, a Cu(II) complex of histamine is reported to possess radiosensitizer activity (see Tonelli, D. et al in 6th Conference on Chemical Modifiers of Cancer Treatment, 1988, p. 2-26), whereas bis(3,5-diisopropylsalicylato)Cu(II) is reported to possess radioprotectant activity (see Sorenson, J. R. J., *J. Med. Chem.*, 27:1747-1749 (1984). Consequently, the presence of a Cu(II) moiety in a complex does not constitute sufficient grounds for predicting that a given complex will possess radiosensitizer activity.

The present invention is based on the finding that certain coordination compounds of copper, namely Cu(II) coordination compounds, render hypoxic cells more sensitive to irradiation.

DESCRIPTION OF THE INVENTION

The Cu(II) compounds contemplated for use herein are selected from compounds having the formula (1):

$$[Cu(II)AB]^Z \quad (1)$$

where
- A represents a bidentate heteroaromatic ligand containing neutral nitrogen donor atoms;
- B represents a bidentate ligand containing neutral or negatively charged oxygen donor atoms; and
- Z represents the charge on the complex; and compounds having the formula (2):

$$[Cu(II)AXY]^{Z^1} \quad (2)$$

where
- A is defined as in (1);
- X and Y are the same or different neutral or negatively charged monodentate ligands; and
- $Z^1$ represents the charge on the complex.

The substituent A may be any bidentate heteroaromatic ligand containing neutral nitrogen donor atoms. Representative of such bidentate heteroaromatic nitrogen containing ligands are phenanthroline, bipyridine, mepirazole or substituted derivatives thereof, e.g. the lower alkyl- or halo-substituted derivatives thereof.

The substituent B may be any bidentate ligand containing neutral or negatively charged oxygen donor atoms. When the oxygen donor ligand B contains an uncharged (neutral) oxygen donor atom, the oxygen is normally in the form of a coordinated water or a carbonyl oxygen. Alternatively, when the oxygen donor atom is negatively charged, it is in the form of a carboxylate, enolate, alkoxide, phenolate or hydroxide.

Representative values for X and Y include water, a halide such as chloride, bromide or iodide, nitrate, acetate, sulfate or hydroxide.

The overall charge of the complex (Z or $Z^1$) may vary from negative, to neutral, to positive, and is the sum of the oxidation state of the copper (+2) and the individual charges on the ligands, including those charges on peripheral, non-coordinating functional groups. Typically, the value of Z or $Z^1$ will range from $-2$ to $+2$.

When the complex is negatively charged, it is associated with appropriate counterions of the type $H^+$, $Na^+$, $K^+$, $NH_4^+$, or the like. When the complex is a cation, appropriate anions include $Cl^-$, $Br^-$, $I^-$, $BF_4^-$, $PF_6^-$, $NO_3^-$, $SO_4^{-2}$, $ClO_4^-$, or the like. These may or may not be coordinated to the Cu atom when in the solid state. All of the above compounds may have an additional solvent molecule, such as $H_2O$ in the fifth or sixth coordination site in the solid state.

The invention contemplates not only the use of the above-noted compounds for use as radiosensitizers but, in addition, pharmaceutical compositions for such use which include the indicated compounds in effective amount as the active radiosensitizing agent, together with a pharmaceutically acceptable vehicle, e.g. a solid or liquid carrier, diluent or excipient therefor. These compositions may take any of the conventional forms for effective administration, e.g. pills, tablets, sterile injectable solutions and the like, containing an effective amount of one or more of the indicated compounds. The amount of active ingredient in such compositions can be widely varied from, for example, 0.001 to 1% or more, based on the total weight of the composition.

The pharmaceutical compositions of the invention may be used in a conventional manner for radiosensitizing purposes in combination with irradiation or the like in the treatment of cancer. Preferably the compound is administered before irradiation in the usual amounts to effect radiosensitization although the administration may also occur concurrently with, or after, the irradiation. The amount of radiosensitizer administered will vary depending on the circumstances although the optimum amount for any particular situation can be routinely determined.

Radiosensitizers for use according to the invention may be evaluated in toxicity and radiosensitization screens. Useful methods of testing include the following:

The compounds are dissolved in Hank's Balanced Salt Solution (HBSS) in concentration of 500, 200, 100 and 10 uM. Drug-induced cytotoxicity is tested using 2 petri dishes per concentration (200 cells/dish) in preplated, log-phase Chinese hamster V-79 cells. A concentration of, advantageously, 100 uM is used for radiosensitization studies. Otherwise, the concentration selected is the maximum allowed with toxicity less than about 50% (surviving fraction=0.5).

Chinese hamster V-79 cells are grown in 60 mm-diameter plastic or glass dishes containing basal medium (Eagle) with HBSS supplemented with 1% penicillin-streptomycin and Hyclone fetal calf serum. The cells are treated on day 6 as unfed, confluent plateau-phase monolayers. Fresh solutions of the compounds to be tested are prepared in HBSS and added to the cells. Irradiation is performed two hours after administration of the drug using a G. E. Maxitron 300 X-ray machine. Plastic dishes are used for aerated cells while glass dishes are used for hypoxic cells. Induction of hypoxia is initiated immediately following administration of the drug and consists of placing the glass dishes containing cells into aluminum chambers, followed by vacuum degassing and purging with nitrogen. The monolayers are trypsinized immediately following irradiation, cell survival is assayed by conventional plating by serial dilution, and colonies are counted 8 days following plating.

By plotting the surviving fraction of cells at a variety of radiation doses, a survival curve is generated. Activity is measured in terms of SER (sensitizer enhancement ratio) which is defined as the ratio of radiation doses in the absence and in the presence of the drug which produce the same biological effect. The higher the SER the more effective the sensitizer. An SER of 1.0 indicates no activity.

Representative examples of compounds which may be used as sensitizers according to the invention are shown in Table I where the following abbreviations are used:

Conc uM = Concentration of the drug in the culture media in uM.

SER(hypox) = Sensitizer enhancement ratio determined in the presence of drug under hypoxic conditions.

SER(oxic) = Defined as in SER(hypox) except the cells are cultured and irradiated in air.

TABLE 1

| Example | Compound | Conc μM | SER hypoxic | SER oxic |
|---|---|---|---|---|
| 1 | | 25 | 1.7 | .9 |
| 2 | | 25 | 1.8 | 1.3 |
| 3 | | 100 | 1.8 | 1.05 |
|   |   | 300 | 2.1 | 1.1 |
| 4 | | 100 | 1.41 | 1.44 |
| 5 | | 100 | 1.71 | 1.09 |

TABLE 1-continued

| Example | Compound | Conc μM | SER hypoxic | oxic |
|---|---|---|---|---|
| 6 | (structure) | 100 | 5.0 | 1.28 |
| 7 | (structure) | 10 | 1.55 | 1.02 |
| 8 | (structure) | 50 | 1.49 | 1.18 |
| 9 | (structure) | 100 | 1.45 | 1.44 |
| 10 | (structure) | 100 | 1.28 | .99 |
| 11 | (structure) | 10 | 4.0 | 1.4 |

The exemplified compounds may be illustrated by the following formula (3):

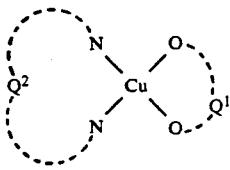

(3)

where
- $Q^1$ represents a 2- or 3-carbon bridging link joining the O atoms; and
- $Q^2$ represents the atoms necessary to complete a polyaromatic ring system wherein the N atoms are in separate rings.

The $Q^1$ and $Q^2$ substituents may comprise unsubstituted hydrocarbon or hydrocarbon substituted to provide substitution external of the chelate ring. Such substitution may comprise single or multiple substituents including unsubstituted hydrocarbon or lower alkoxy, hydroxy, halogen, carbonyl, amino, carboalkoxy or polyether, or hydrocarbon substituted with, for example, lower alkyl, lower alkoxy, hydroxy, halogen, carbonyl, amino, carboalkoxy or polyether. The $Q^1$ and $Q^2$ substituents may also include additional N or O atoms in the rings.

The compounds referred to in Table 1 were prepared as follows:

EXAMPLE 1

[(Malonato(2-)(1,10-Phenanthroline) Copper(II)]Dihydrate

This compound was prepared according to the method of W. L. Kwik et al in *Inorganic Synthesis*, XXI:114 (1982) edited by John P. Fackler, Jr., published by John Wiley and Sons.

A sample of 1,10-phenanthroline monohydrate (3.96 g, 20 mmole) in 20 mL ethanol was added to a solution of copper(II) chloride dihydrate (3.40 g, 20 mmole) in 40 mL ethanol. A suspension of a green-blue solid developed immediately. A solution of malonic acid (2.08 g, 20 mmole) in 50 mL ethanol was added to the stirred suspension, followed by a gradual addition of 1.0M ammonium hydroxide solution until a blue precipitate was formed. This solid was separated by filtration and washed with several 10 mL portions of distilled water as well as ethanol. The product was recrystallized from water/methanol (3:2) mixture, and the bright blue crystals obtained were air dried and finally dried in vacuo. Yield was 5.0–5.4 g (70–75% based on $CuCl_2.2H_2O$).

Analysis for $C_{15}H_{10}N_2O_4Cu$;: Calc.: Cu, 16.60; C, 47.20; H, 3.70; N,7.30. Found: Cu, 16.80; C, 46.90; H, 3.80; N, 7.20.

EXAMPLE 2

[Salicylato(1-)(1,10-Phenanthroline) Copper(II)]Chloride

A solution of the sodium salt of salicylaldehyde prepared by adding 1N NaOH to an aqueous emulsion of salicylaldehyde (1.2 g, 0.01 mole) was added to a solution of $Cu(phen)Cl_2$(3 g 0.095 mole) prepared as in Example 1. After an hour, the green precipitate was collected and dried in vacuo.

Analysis for $C_{19}H_{13}N_2ClCuO_2$: Calc.: C, 57.01; H, 3.27; N, 7.00. Found: C, 56.46; H, 3.08; N, 7.17.

EXAMPLE 3

[Malonato(2-)(2,2-Dipyridyl)Copper(II)]

A solution of 15.1 g (0.097 mol) of 2,2'-bipyridine in 75 ml MeOH is added to a solution 16.5 g (0.097 mol) of $CuCl_2.2H_2O$ at room temperature. After 10 minutes of stirring, the turquoise [(2,2'-dipyridyl)(dichloro)Cu(II)] is collected, washed with MeOH and $Et_2O$ and air dried (yield 24.9 g).

A solution of 68 ml 1N.NaOH is added to 3.54 g (0.034 mol) malonic acid in 100 ml. This solution is added to a solution 10 gm of (2,2'-dipyridyl)(dichloro)-Cu(II) dissolved in 500 ml $H_2O$. The blue precipitate was collected, washed with $H_2O$ and dried in vacuo to yield 9.84 g of Malonato (2)-(2,2'-dipyridyl)Cu(II).2-$H_2O$.

Analysis for $C_{13}H_{14}N_2O_6Cu$;: Calc.: C,43.64; H, 3.54; N, 7.83. Found: C,44.05; H, 3.92; N, 7.74.

EXAMPLE 4

[(1,1-Cyclobutanedicarboxylate(2-) (2,2'-Dipyridyl)Copper(II)

This compound was prepared as in Example 5 (below) substituting 1,1-cyclobutane-dicarboxylic acid for tartronic acid.

Analysis for $[(C_{16}H_{14}O_4N_2)Cu]$: Calc.: C, 53.11; H, 3.90; N, 7.74. Found: C, 53.16; H, 3.87; N, 7.72.

EXAMPLE 5

[(Tartranato(2-))(2,2'-Dipyridyl) Copper(II)].$\frac{1}{2}H_2O$

To a stirred solution of $Cu(bipy)Cl_2$ (3.0 g, 10.3 mmol), prepared as in Example 3, in 150 cm$^3$ of water was added a stirred solution of Tartronic acid (1.24 g, 10.3 mmol), neutralized with 2 equivalents of sodium hydroxide, in 30 cm$^3$ of water. The solution was reduced to $\frac{1}{2}$ of its volume under reduced pressure and, after 1 hour, a blue solid precipitated. The blue solid, [(2,2'-bipyridyl)(tartronato)-copper(II)].$\frac{1}{2}H_2O$, was collected by filtration, washed with water and diethyl ether, and dried in vacuo.

EXAMPLE 6

[(Tartranato(2-))(4,4'-Dimethyl-2,2'-Bipyridyl)Copper-(II)].$H_2O$

This compound was prepared as in Example 5 substituting [(4,4'-dimethyl-2,2'-bipyridyl)copper(dichloride)] for 2,2'-bipyridylcopperdichloride.

Analysis for $C_{15}H_{14}N_2O_5Cu.H_2O$: Calc.: C, 46.94; H, 4.20; N, 7.30. Found: C, 47.02; H, 4.21; N, 7.25.

EXAMPLE 7

[(2,2'-Bipyridyl)(2.5-Pentanedionato)Copper]Chloride Hydrate 4.0 g of $Cu(bipy)Cl_2$ (14 mmol) was dissolved in water (200 ml). To this blue solution was added, 1.4 g of 2,4-pentanedione (14 mmol) dissolved in water (15 ml) with 1 equivalent of NaOH. The deep blue solution was treated with excess $NH_4PF_6$. The resulting solid was collected and stirred in 100 ml of water with excess anion exchange resin (Dowex 1-X8 in Cl form) to yield a clear blue solution. The solution was freeze dried to yield 2.5 g of blue $C_{15}H_{15}ClN_2O_5Cu.H_2O$. Yield=48%.

| Analysis: | % Calc | % Found |
|---|---|---|
| C | 48.40 | 48.50 |
| H | 4.61 | 4.34 |
| N | 7.53 | 7.48 |

EXAMPLE 8

[(3-(3-Methylproprionate)2,4-Pentanedionato)(2,2′-Bipyridyl)Copper(II)]BF$_4$

This compound was prepared as in Example 5 substituting methyl-4-acetyl-5-oxohexanoate for tartronic acid, and using 1 equivalent of sodium hydroxide to neutralize the ligand which was dissolved in 10 cm$^3$ of methanol. Sodium tetrafluoroborate (5 g, 45 mmol) was added to the clear blue solution and a brownish/purple solid precipitated. The solid was filtered, washed with a minimal amount of water, and dried in vacuo.

Analysis for C$_{19}$H$_{21}$O$_4$N$_2$CuBF$_4$: Calc.: C, 46.41; H, 4.30; N, 5.70. Found: C, 46.72; H, 4.27; N, 5.75.

EXAMPLE 9

[(2,2′-Bipyridyl)(Maltolato)Copper]BF$_4$ 0.76 g of Cu(bpy)Cl$_2$ (2.6 mmol) was dissolved in water (50 ml). To this blue solution was added 0.33 g of maltol dissolved in 15 ml of water with 0.25 g NaHCO$_3$. The resulting blue-green solution was filtered and the filtrate treated with NaBF$_4$ (2 g). This caused a microcrystalline green precipitate to form. The solid was collected, washed with 95% ETOH and dried in vacuo. Yield=1.1 g, 96%.

| Analysis: | % Calc | % Found |
|---|---|---|
| C | 44.52 | 44.45 |
| H | 3.04 | 3.00 |
| N | 6.49 | 6.35 |

EXAMPLE 10

[(Oxalato(20))(2,2′-Bipyridyl)Copper(II)]

This compound was prepared using the process of Example 5 but substituting oxalic acid for tartronic acid.

Analysis for C$_{12}$H$_8$N$_2$O$_4$Cu: Calc.: C, 46.83; H, 2.62; N, 9.10. Found: C, 46.85; H, 2.39; N, 9.05.

EXAMPLE 11

[(Malonato(2-))(Meperizole)Copper(II)]

To a stirring solution of (meperizole)CuCl$_2$ (0.82 g, 2.22 mmol) in 20 cm$^3$ of water was added a solution of malonic acid (0.23 g, 2.22 mmol) and NaOH (0.177 g, 4.44 mmol) dissolved in 10 ml of ethanol. The solution retained is green in color so NH$_4$OH (1 ml) was added dropwise until the color changed to blue. Then the solution was left to slowly evaporate until the volume was approximately 10 ml. The blue solid was then filtered off and air dried.

Analysis for C$_{14}$H$_{16}$N$_4$O$_6$Cu.3H$_2$O: Calc.: C, 37.05; H, 4.89; N, 12.34. Found: C, 36.65; H, 4.87; N, 12.04.

The foregoing examples are illustrative of the case where A is phenanthroline, bipyridine or mepirazole or substituted derivatives thereof while B represents malonic acid, acac, salicylaldehyde, 2-hydroxy-pyridine-N-oxide or substituted derivatives thereof.

Other compounds contemplated for use herein include those shown in Table 2 below, all of which can be prepared and used in the manner referred to earlier:

TABLE 2$^a$

Compounds

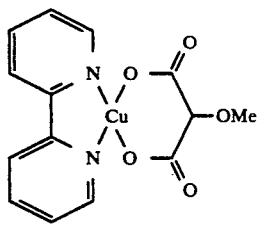

i

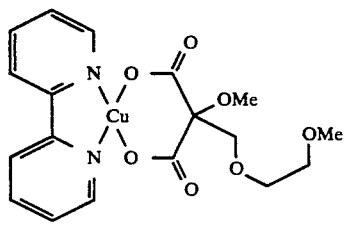

ii

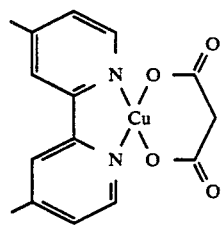

iii

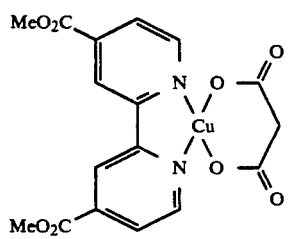

iv

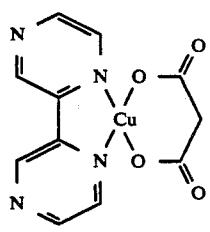

v

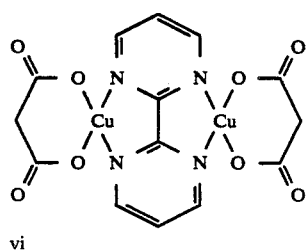

vi

TABLE 2a-continued

Compounds

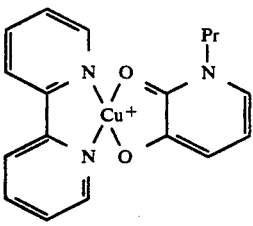
vii

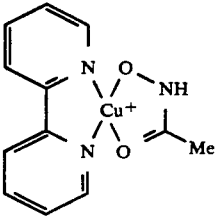
viii

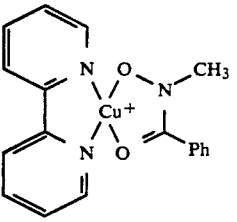
ix

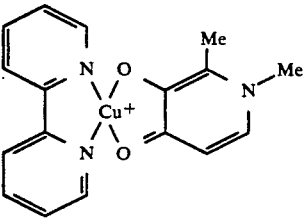
x

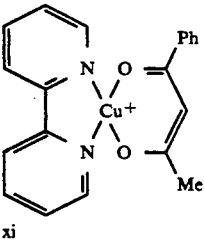
xi

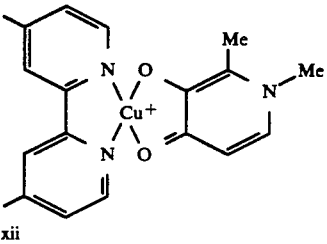
xii

TABLE 2a-continued

Compounds

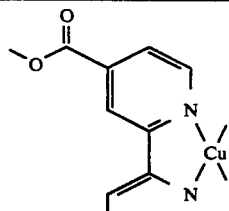
xiii

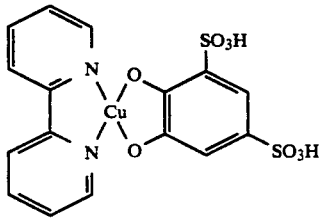
xiv

<sup>a</sup>Counterions not shown.

A representative subgroup of compounds for use herein may also be structurally represented by formula (4):

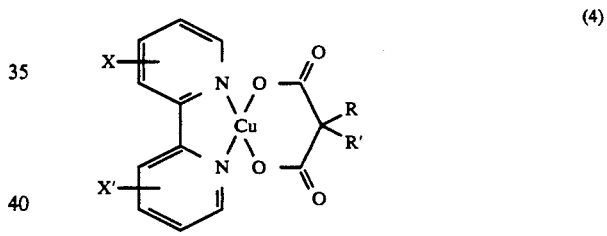

(4)

where
X and X', which may be the same or different, stand for hydrogen; $C_1$–$C_6$ straight or branched alkyl; an ether group such as —$(CH_2O)_n(CH_2CH_2O)_mZ$ or $(CH_2CH_2O)_mZ$ where n is 0–1, m is 0–2, Z is H or $C_1$–$C_4$ straight or branched alkyl; an amine group such as —$NZ_2$ where Z is defined above; an ester group such as —$CO_2Z$ where Z is defined above; amides such as —C(O)NZZ' where Z and Z' are the same or different and defined as Z above; halide such as F, Cl, Br or I; or $NO_2$;

R and R, which may be the same or different, stand for hydrogen; $C_1$–$C_6$ straight or branched alkyl; an ether group such as —$(CH_2O)_n(CH_2CH_2O)_mZ$ where n, m and Z are defined above; halide; or $NO_2$ or R is defined as above and R' is OZ, where Z is as defined above.

It will be recognized from the foregoing that the invention is not limited to the examples given above but instead contemplates the use of any of the compounds of formula (1) or formula (2) as radiosensitizers in the manner disclosed herein. Accordingly, the scope of the invention is defined in the following claims wherein:

We claim:

1. A pharmaceutical composition containing a radiosensitizing amount of a Cu (II) compound selected from the group consisting of compound having the formula (3):

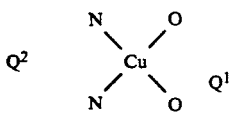

(3)

where
- $Q^1$ represents a 2- or 3-carbon bridging link joining the O atoms; and
- $Q^2$ represents the atoms necessary to complete a two or three ring system wherein the N atoms are in separate rings; and wherein $Q^1$ and $Q^2$ are unsubstituted hydrocarbon groups or hydrocarbon substituted with lower alkoxy, hydroxy, halogen, carbonyl, amino, carboalkoxy or polyether and the $Q^1$ and $Q^2$ substituents may also include additional N or O atoms in the ring and a pharmaceutically acceptably vehicle therefor.

2. A pharmaceutical composition containing a radiosensitizing amount of a Cu (II) compound selected from the group consisting of
[(malonato(2-)(1,10-phenanthroline)copper(II)]dihydrate; [salicylato(1-)(1,10-phenanthroline)copper(II)]chloride; [malonato(2-)(2,2-dipyridyl)copper(II)]; [(1,1-cyclobutanedicarboxylate(2-))(2,2'-dipyridyl)copper(II); [(tartranato(2-))(2,2'-dipyridyl)copper(II)].½H$_2$O; [(tartranato(2-))(4,4'-dimethyl-2,2'-bipyridyl)copper(II)].H$_2$O; [(2,2'-bipyridyl)(2,5-pentanedionato)copper]chloride hydrate; [(3-(3-methylpropionate)2,4-pentanedionato)(2,2'-bipyridyl)copper(II)]BF$_4$; [(2,2'-bipyridyl)(maltolato)copper]BF$_4$; [(oxalato(20))(2,2'-bipyridyl)copper(II)]; and [(malonato(2-)(meperizole)copper(II)]
and a pharmaceutically acceptable vehicle therefor.

* * * * *